(12) United States Patent
Palmer et al.

(10) Patent No.: US 7,608,111 B2
(45) Date of Patent: Oct. 27, 2009

(54) METHODS AND DEVICES FOR RESURFACING THE WRIST JOINT

(75) Inventors: Andrew K. Palmer, East Syracuse, NY (US); Jason I. Partin, Encinitas, CA (US)

(73) Assignee: Biomet Manufacturing Corp., Warsaw, IN (US)

( * ) Notice: Subject to any disclaimer, the term of this patent is extended or adjusted under 35 U.S.C. 154(b) by 66 days.

(21) Appl. No.: 11/626,107

(22) Filed: Jan. 23, 2007

(65) Prior Publication Data

US 2007/0185582 A1 Aug. 9, 2007

Related U.S. Application Data

(60) Provisional application No. 60/749,766, filed on Jan. 24, 2006.

(51) Int. Cl.
*A61F 2/42* (2006.01)
(52) U.S. Cl. .................. 623/21.14; 623/21.12
(58) Field of Classification Search ............. 623/21.11, 623/21.12, 21.13, 21.14; *A61F 2/42*
See application file for complete search history.

(56) References Cited

U.S. PATENT DOCUMENTS

| | | | |
|---|---|---|---|
| 3,879,767 A | 4/1975 | Stubstad | |
| 4,645,505 A | 2/1987 | Swanson | |
| 4,714,476 A * | 12/1987 | Ranawat et al. | 623/21.12 |
| 5,405,401 A * | 4/1995 | Lippincott et al. | 623/21.15 |
| 5,683,466 A * | 11/1997 | Vitale | 623/21.15 |
| 6,746,486 B1 * | 6/2004 | Shultz et al. | 623/21.12 |
| 7,291,175 B1 * | 11/2007 | Gordon | 623/21.19 |
| 2005/0004675 A1 * | 1/2005 | Shultz et al. | 623/21.14 |
| 2006/0036330 A1 | 2/2006 | Shultz et al. | |

FOREIGN PATENT DOCUMENTS

| | | |
|---|---|---|
| DE | 100 43 107 | 9/2002 |
| DE | 10237016 | 2/2004 |
| EP | 0 034 192 | 8/1981 |
| EP | GB2269752 | 2/1994 |
| FR | 2660856 | 10/1991 |
| WO | WO-92/00709 | 1/1992 |
| WO | WO 2006/048520 | 5/2006 |
| WO | WO-2007047230 | 4/2007 |

OTHER PUBLICATIONS

Universal Total Wrist Implant System at www.visitkmi.com/totwrist.html.
European Search Report for EP 07 25 3509 mailed Jan. 14, 2008.

* cited by examiner

*Primary Examiner*—David Isabella
*Assistant Examiner*—Yashita Sharma
(74) *Attorney, Agent, or Firm*—Harness, Dickey (57) ABSTRACT

A wrist arthroplasty system comprising a carpal implant for resurfacing carpal bones that is at least substantially arcuate in shape from a first end to a second end. The carpal implant includes a first carpal engaging surface, a second carpal engaging surface, a first carpal articulating surface, and a second carpal articulating surface. The first carpal engaging surface has an arcuate concave shape that at least substantially corresponds to a natural shape of a scaphoid bone. The second carpal engaging surface at least substantially corresponds to a natural shape of a lunate bone. The first carpal articulating surface is opposite to the first carpal engaging surface. The first carpal articulating surface has an arcuate convex shape. The second carpal articulating surface is opposite to the second carpal engaging surface.

20 Claims, 7 Drawing Sheets

METHODS AND DEVICES FOR RESURFACING THE WRIST JOINT

CROSS-REFERENCE TO RELATED APPLICATIONS

This application claims the benefit of U.S. Provisional Application No. 60/749,766, filed on Jan. 24, 2006. The disclosure of the above application is incorporated herein by reference.

FIELD

The present disclosure generally relates to orthopedic implants. In particular, the present disclosure relates to a wrist arthroplasty system.

BACKGROUND

The statements in this section merely provide background information related to the present disclosure and may not constitute prior art.

Current total joint replacement implants for the wrist require removing large sections of bone and soft tissues due to the large size of the implants. Current implants also require bone purchase or bone cement for stability. Further, implantation of current wrist implants requires making large incisions in the patient to provide the surgeon with the access required to ensure proper alignment of the implants.

Consequently, patients can experience long operating room times, lengthy recovery, and reduced mobility. Revision surgeries are challenging because substantial bone has been removed, and there may not be a salvage procedure other than fusion of the joint. Partial wrist replacements still require bone removal and soft tissue damage during surgery, leading to joint instability and few revision options.

Thus, there is a need for an implant system that treats all or a portion of the joint surface with minimal damage to bone or soft tissues, yet is mechanically stable and secure to the bone.

SUMMARY

The present disclosure provides for a wrist arthroplasty system comprising a carpal implant for resurfacing carpal bones that is at least substantially arcuate in shape from a first end to a second end. The carpal implant includes a first carpal engaging surface, a second carpal engaging surface, a first carpal articulating surface, and a second carpal articulating surface. The first carpal engaging surface has an arcuate concave shape that at least substantially corresponds to a natural shape of a scaphoid bone. The second carpal engaging surface at least substantially corresponds to a natural shape of a lunate bone. The first carpal articulating surface is opposite to the first carpal engaging surface. The first carpal articulating surface has an arcuate convex shape. The second carpal articulating surface is opposite to the second carpal engaging surface.

The present disclosure further provides for a wrist arthroplasty system comprising a carpal implant and a radial implant. The carpal implant is for resurfacing carpal bones and has a concave, arcuate carpal engaging surface that at least substantially corresponds to the natural shape of carpal bones and a convex, arcuate carpal articulating surface that is opposite to the engaging surface. The radial implant is for resurfacing a radius bone having a concave, radial articulating surface operable to articulate with the carpal articulating surface. A convex radial engaging surface is opposite to the radial articulating surface. A first radial stabilizing fin extends from the radial engaging surface.

The present disclosure also provides for a wrist arthroplasty system comprising a unitary carpal implant and a unitary radial implant. The unitary carpal implant has a main carpal body with a carpal engaging surface on a first side of the main body and a carpal articulating surface on a second side of the main body. The first side is opposite to the second side. The unitary radial implant has a main radial body with a radial engaging surface on a first side of the main radial body and a radial articulating surface on a second side of the main radial body. The first side is opposite to the second side. The carpal articulating surface articulates directly with the radial articulating surface.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
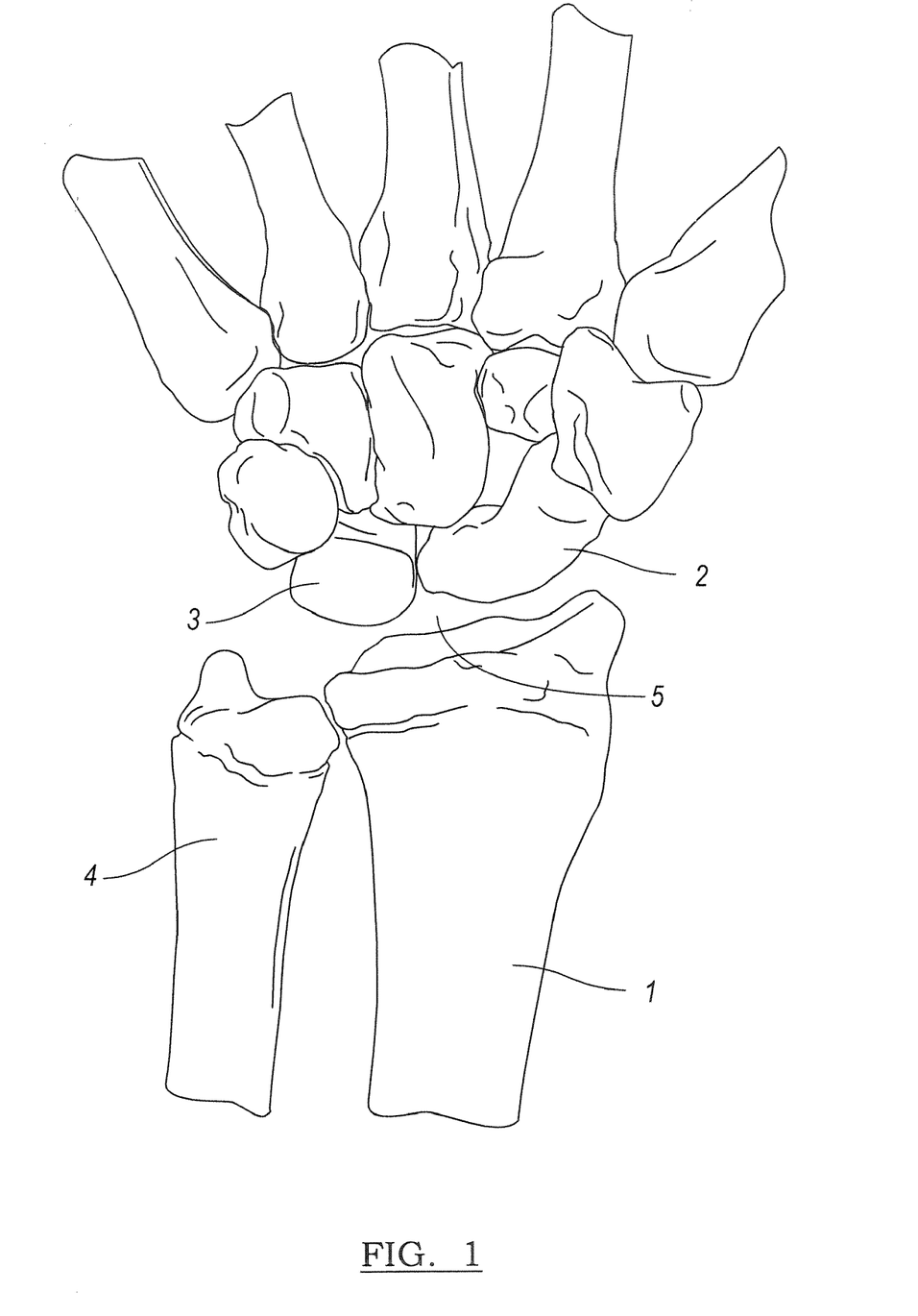
FIG. 1 illustrates bones of a typical human wrist.

FIG. 1 illustrates the primary bones of a human forearm and wrist. The bones of the forearm include a radius 1 and an ulna 4. The radius 1 articulates against a scaphoid bone 2 and a lunate bone 3, which are each carpal bones. Joint space 5 is defined as an area between the radius 1 and the carpal bones 2 and 3, or between the articulating surfaces of the implants described herein for the radius 1 or carpal bones 2 and 3.

Figures 2A, 2B, 2C:
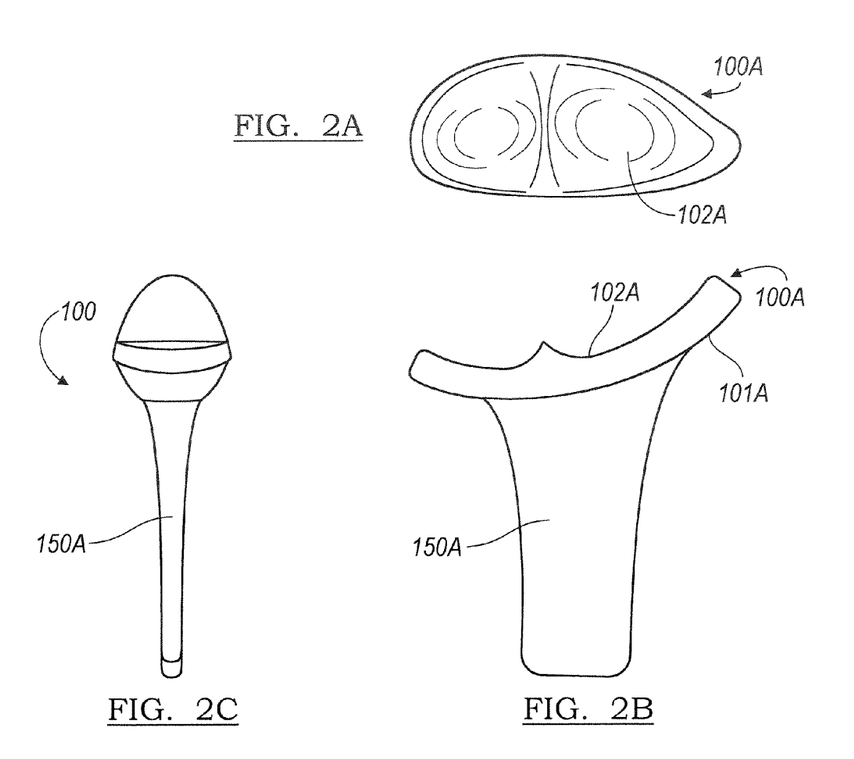
FIG. 2A illustrates an upper surface of a radial implant according to the present teachings.
FIG. 2B is a plan view of the radial implant of FIG. 2A.
FIG. 2C is a side view of the radial implant of FIG. 2A.

FIG. 2 illustrates a resurfacing implant for the radius 1. FIG. 2A illustrates an articulating surface 102A of a radial implant 100A. The radial implant 100A can have tapered edges to prevent sharp contact with soft tissue. FIG. 2B illustrates a frontal plan view of the radial implant 100A, the articulating surface 102A, and the static surface 101A. FIG. 2C is a side view of the radial implant 100A, illustrating a stabilizing fin 150A that fits into the radius 1.

The articulating surface 102A has at least one generally concave surface facing the joint space 5, and can have one or more points of concavity generally shaped and oriented to match the carpal bones 2 and 3. The static surface 101A contacts the cartilage, bone, or tissue of the radius 1, and is shaped to generally fit within the radius 1. The static surface 101A can also have a more consistent shape that could be cut or reamed into the radius 1. An additional component can be a polymer or bone cement layer between the static surface 101A and the radius 1 to fill voids and provide a more uniform contacting surface.

The stabilizing fin 150A can be a fixed component of the radial implant 100A or a separate attachment connected during assembly of the implant 100A. The stabilizing fin 150A can also be inserted into the intramedullary canal. In another embodiment, the fin 150A can transition into a rod that secures in the intramedullary canal. In another embodiment, the intramedullary rod can be secured directly to the radial implant.

Figure 3:
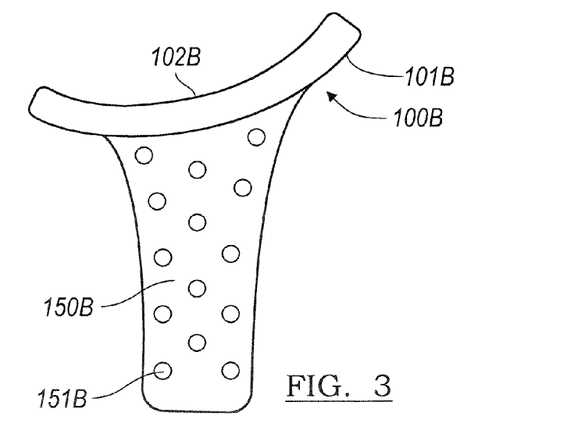
FIG. 3 is a plan view of an additional radial implant in accordance with the present teachings.

FIG. 3 illustrates an additional embodiment of the radial implant 100A at reference numeral 100B. The articulating surface 102B can have a smooth, generally concave surface without specific contours for the carpal bones. Other embodiments include prongs or hooks extending from or near the articulating surface 102B dorsally or anteriorly to wrap around the distal aspect of the radius 1. Dorsally, the prongs or hooks can be aligned between ligaments, including but not limited to the radioscapholapitate ligament, the short radiolunatea ligament, the long radiolunate ligament, and the ulnal lunate ligament. The stabilizing fin 150B can have cutouts 151B to allow a mechanical lock when bone or tissue grows into the cutouts 151B. Alternatively, the cutouts 151B can be filled with bone paste, absorbable polymers, collagen, or any other substance to facilitate bone growth. Alternatively, the stabilizing fin 150B can be porous, coated, or otherwise textured to facilitate bone growth, such as applying a titanium using plasma spray or sintered beading, or applying a ceramic or polymer coating.

Figure 4:
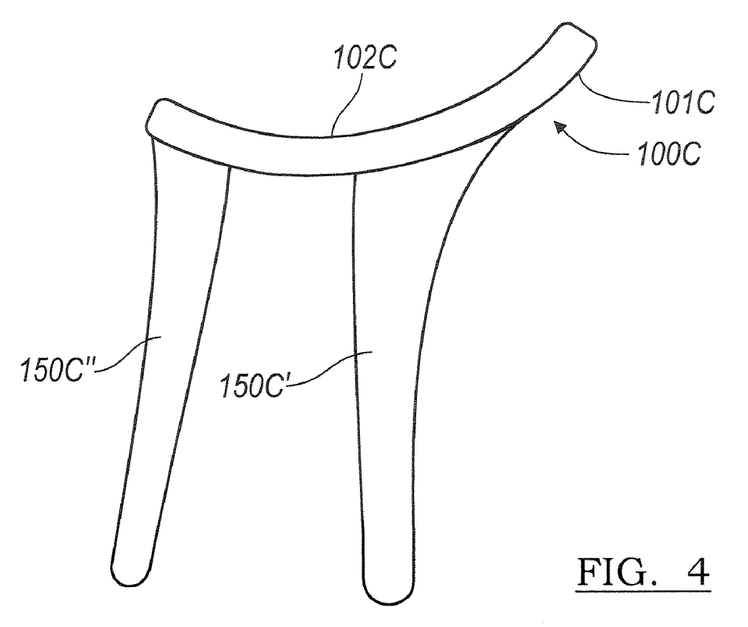
FIG. 4 is a plan view of a further radial implant in accordance with the present teachings.

FIG. 4 illustrates an additional embodiment of the radial implant at 100C. The radial implant 100C includes a first stabilizing fin 150C' and a second stabilizing fin 150C" spaced apart from the first stabilizing fin 150C'. The first and second stabilizing fins 150C' and 150C" are positioned to engage strong bone in the radius 1, such as the cortical shell. The stabilizing fins 150C' and 150C" can be tapered to transition forces from the radial implant 100C into the radius 1. One or more support members can connect the stabilizing fins 150C' and 150C" to provide additional stability.

Figure 5:
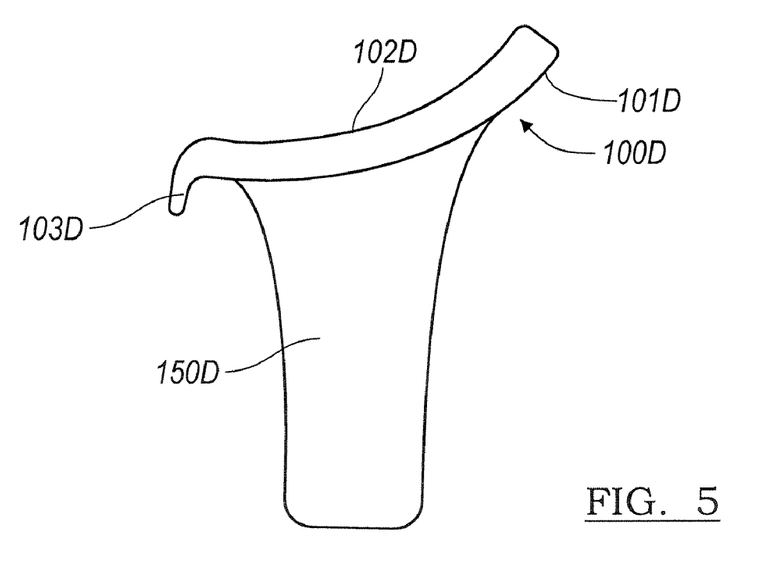
FIG. 5 is a plan view of another radial implant in accordance with the present teachings.

FIG. 5 illustrates an additional embodiment of the radial implant at 100D. The radial implant 100D includes a protrusion 103D for articulation between the radius 1 and ulna 4. The protrusion 103D can function as a spacer between the radius 1 and ulna 4 when there is arthritis or damage at this joint. Alternatively, the protrusion 103D can secure to the ulna 4 or a separate implant in the ulna 4 and have a hinge or pivoting mechanism to allow motion between the radius 1 and ulna 4. Alternatively, the protrusion 103D can be any attachment feature for ulna implants.

Figure 6A:
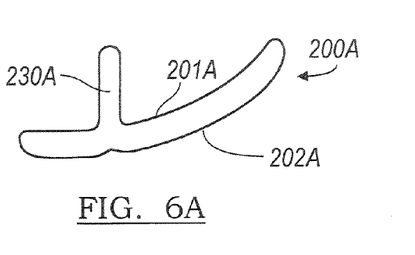
FIG. 6A is a plan view of a carpal implant in accordance with the present teachings.
Figure 6B:
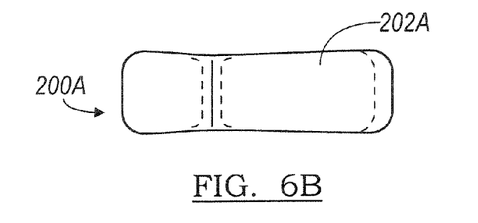
FIG. 6B is a bottom view of the carpal implant of FIG. 6A.
Figure 6C:
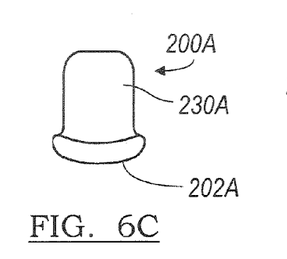
FIG. 6C is a side view of the carpal implant of FIG. 6A.

FIG. 6 illustrates a resurfacing implant for the carpal bones 3 and 4 of the wrist joint at reference numeral 200A. FIG. 6A illustrates a frontal plan view of the carpal implant 200A having an articulating surface 202A and a static surface 201A. The carpal implant 200A can have tapered edges to prevent sharp contact with soft tissues. FIG. 6B illustrates a bottom view of the articulating surface 202A. FIG. 6C is a side view of the carpal implant 200A illustrating a spacer 230A sized to fit between the scaphoid 2 and the lunate 3.

The articulating surface 202A has at least one generally convex surface facing the joint space 5, and can have one or more points of convexity generally shaped and oriented to match the radius 1. The static surface 201A can contact the cartilage, bone, or tissue of the carpal bones 2 and 3, and is shaped to generally fit the carpal bones 2 and 3. An additional component, such as a polymer or bone cement layer can be positioned between the static surface 201A and the radius 1 to fill voids and provide a more uniform contacting surface.

The static surface 201A and the spacer 230A maintain stability by being shaped to closely fit the carpal bones 2 and 3. In another embodiment, the spacer 230A has one or more holes to facilitate alignment of stabilizing pins, rods, or screws. In another embodiment, the static surface 201A or spacer 230A are porous or coated with a porous material to facilitate bone growth for stability. In yet another embodiment, the static surface 201A has a shape that could be cut or reamed into the carpal bones 2 and 3 for a precise fit.

Figure 7:
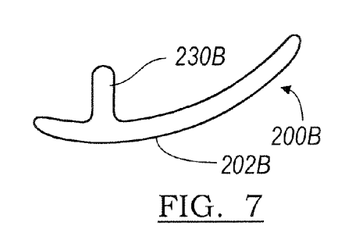
FIG. 7 is a plan view of an additional carpal implant in accordance with the present teachings.

FIG. 7 illustrates an additional embodiment of the carpal implant 200A at reference numeral 200B. The carpal implant 200B includes an articulating surface 202B that has one generally convex surface that can be shaped to fit the radius of the radial implant 100. The spacer 230B can be used to separate the scaphoid 2 and lunate 3. In another embodiment, the spacer 230B can contour along the carpal bones but not enter the joint space between the scaphoid and lunate. In another embodiment, the spacer 230B can be omitted. In another embodiment, the carpal implant 200B can be sized to fit only one carpal bone.

Figure 8:
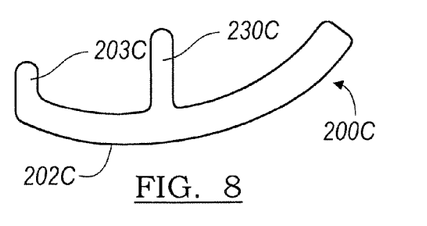
FIG. 8 is a plan view of a further carpal implant in accordance with the present teachings.

FIG. 8 illustrates another embodiment of the carpal implant 200A at reference numeral 200C. The carpal implant 200C includes a stabilizing component 203C that secures one or more edges of one or more carpal bones to help secure the carpal implant 200C. The stabilizing component 203C can have holes or cutouts for rods, pins, or screws that secure to the carpal bones.

Figure 9A:
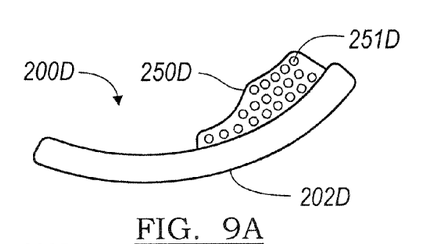
FIG. 9A is a plan view of another carpal implant in accordance with the present teachings.
Figure 9B:
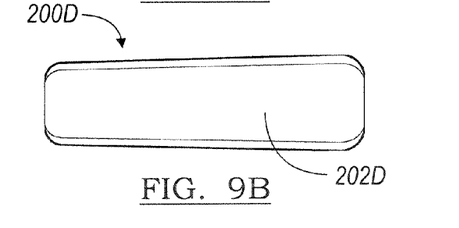
FIG. 9B is a bottom view of the carpal implant of FIG. 9A.
Figure 9C:
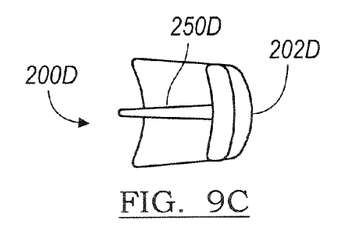
FIG. 9C is a side view of the carpal implant of FIG. 9A.

FIG. 9 illustrates an additional embodiment of the carpal implant 200A at reference numeral 200D. The carpal implant 200D includes a stabilizing fin 250D. FIG. 9A is a frontal plan view illustrating the stabilizing fin 250D that would enter the scaphoid 2. The stabilizing fin 250D has one or more cutouts 251D for stability from bone or tissue growth. In another embodiment, the fin 250D is textured or porous, or coated with a textured or porous material. In another embodiment, the fin 250D is smooth. FIG. 9B illustrates a bottom view of the carpal implant 200D articulating surface 202. FIG. 9C illustrates a side view of the carpal implant 200D with the stabilizing fin 250.

Figure 10:
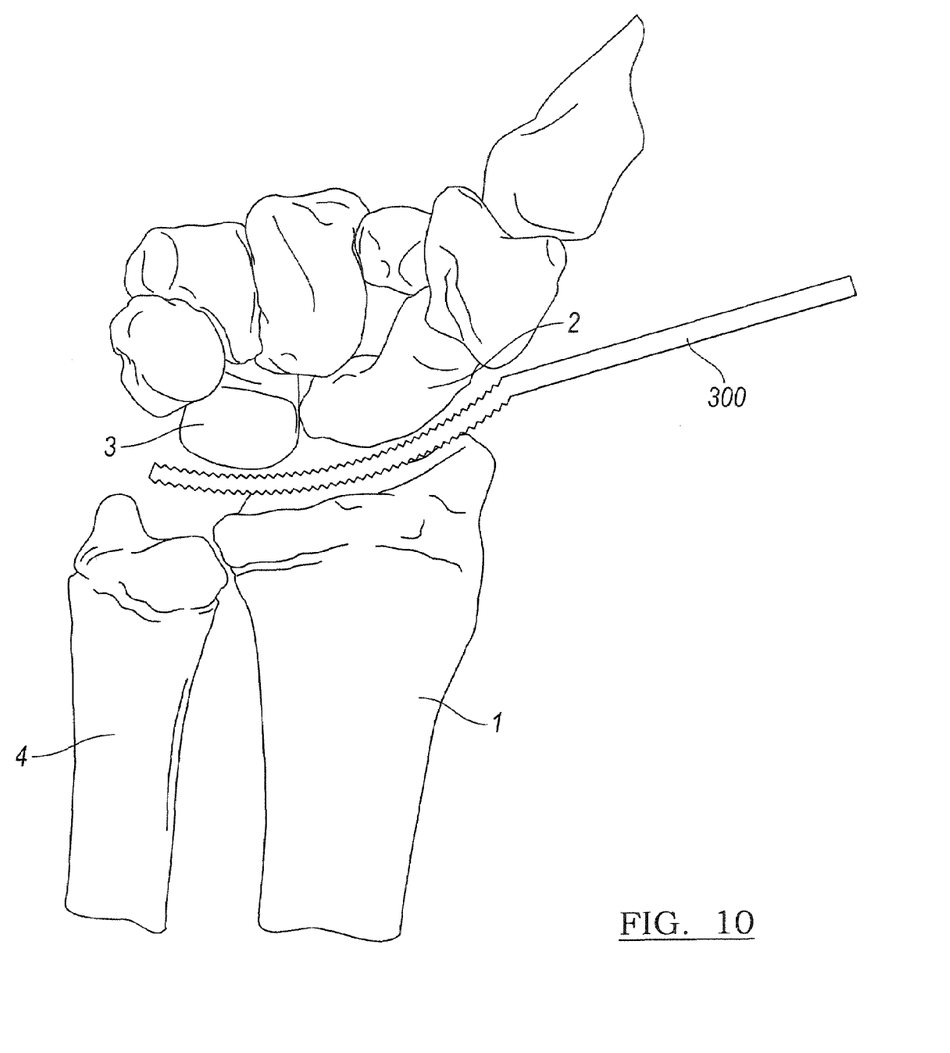
FIG. 10 illustrates the preparation of the wrist joint of FIG. 1 to receive a carpal and/or radial implant according to the present teachings.

FIG. 10 illustrates a reaming device 300 to prepare the radius 1 and the carpal bones 2 and 3 to receive one of the radial implants 100A-D and/or one of the carpal implants 200A-D. The reaming device 300 is textured to remove cartilage or other tissues. In the embodiment illustrated, the reaming device 300 is shaped to create a single radius of curvature for both the radius 1 and carpal bones 2 and 3. In another embodiment, the reaming device 300 can create multiple points of curvature. In another embodiment, the reaming device 300 can be designed with texture only on certain areas, allowing the surgeon to prepare only the radius 1, or only the carpal bones 2 and 3, or only one carpal bone, or a combination thereof.

Figure 11:
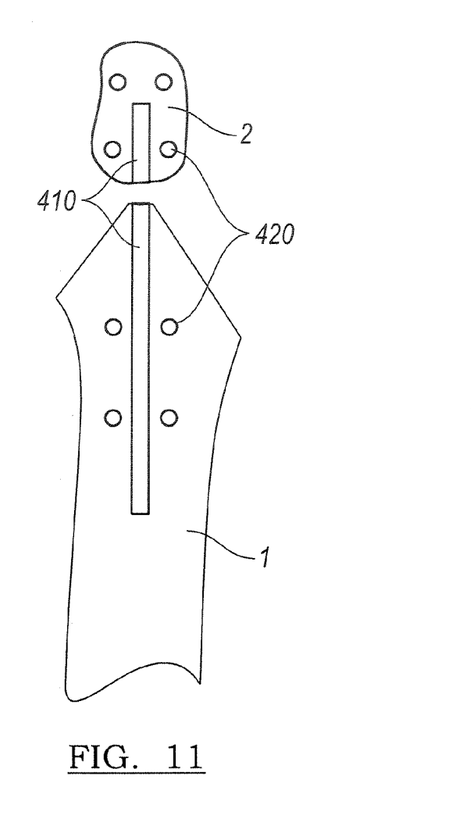
FIG. 11 is a side view of the radius and scaphoid of the human wrist of FIG. 1 prepared in accordance with the present teachings to receive a radial implant in accordance with the present teachings and a carpal implant in accordance with the present teachings.

FIG. 11 illustrates a side view of the radius 1 and scaphoid 2 with a slot 410 cut for the stabilizing fins 150 and 250 to enter the radius 1 and scaphoid 2. Alignment of the slot 410 is controlled by a fixture or jig that can be oriented using alignment holes 420. A saw can create the slot 410 to receive the implants 100A-D and 200A-D. An additional component can be pre-shaped bone graft or bone growth material to fit inside one or more of the slots 410.

Figure 12:
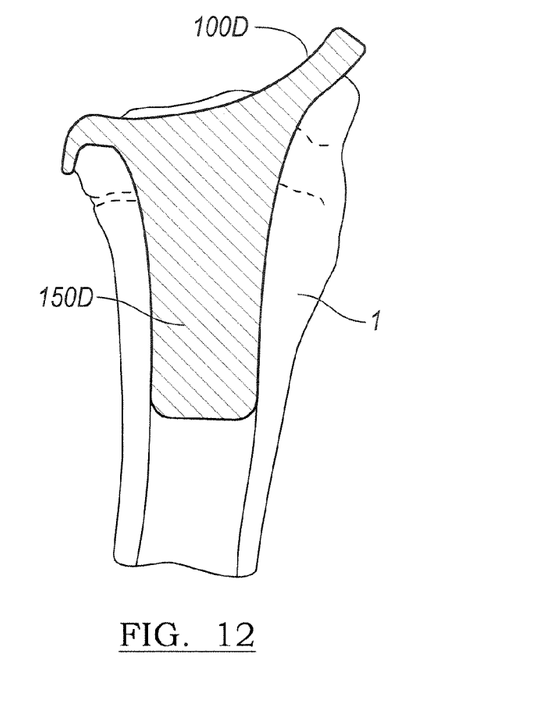
FIG. 12 is a cross-sectional view of the radial implant of FIG. 5 implanted in the radius.

FIG. 12 illustrates a cross-sectional view of the radial implant 100D for resurfacing the radius 1, with the stabilizing fin 150D implanted inside the radius 1.

Figure 13:
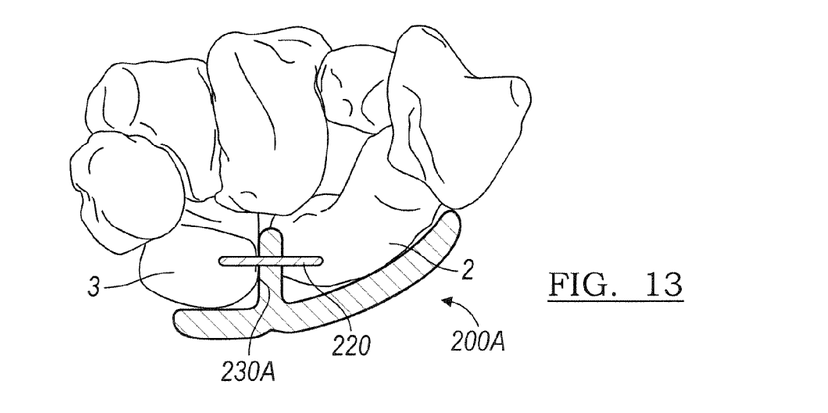
FIG. 13 is a cross-sectional view of the carpal implant of FIG. 6A implanted in the wrist of FIG. 1.

FIG. 13 illustrates a cross-sectional view of the carpal implant 200A resurfacing the scaphoid 2 and lunate 3 with one or more stabilizing pins or screws 220 extending through the spacer 230A and into the carpal bones 2 and 3.

Figure 14:
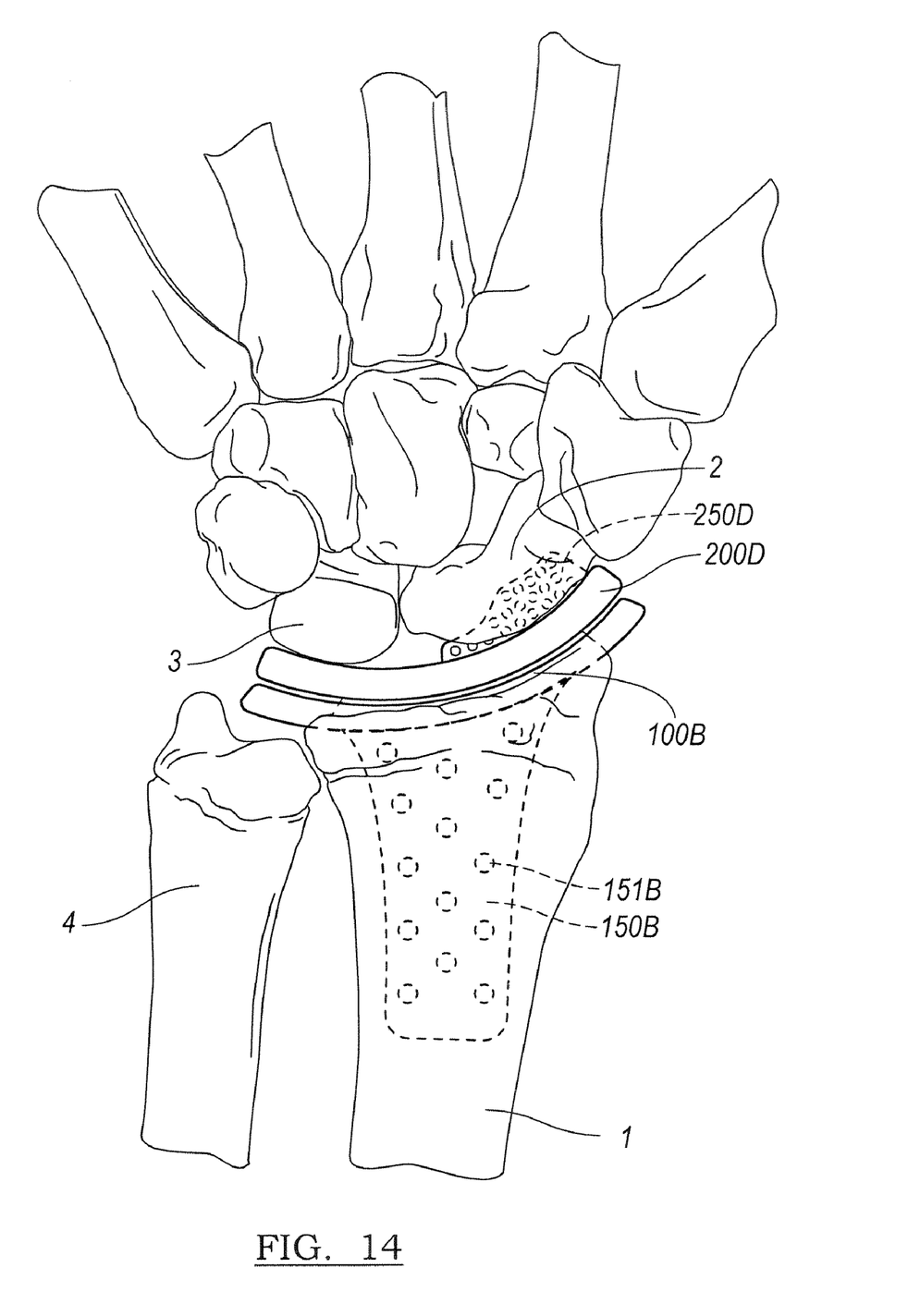
FIG. 14 illustrates the carpal implant of FIG. 9A and the radial implant of FIG. 3 implanted in the wrist of FIG. 1.

FIG. 14 illustrates the radial implant 100B and the carpal implant 200D combined to form a total wrist resurfacing implant. The radial stabilizing fin 150B has one or more holes 151B to allow bone growth and the carpal implant 200D is secured by a carpal stabilizing fin 250D.

While FIG. 14 illustrates metal on metal articulation with the radial implant 100B articulating with the carpal implant 200D, it is not necessary that the implants 100B and 200D articulate with each other or that both be present. For example, the radial implant 100B alone, as well as radial implants 100A, 100C, and 100D, can be implanted and can articulate with the carpal bones 2 and 3. Similarly, the carpal implant 200D alone, as well as carpal implants 200A-200C, can be implanted and can articulate with the radius 1. Further, the static surfaces 101A-101D are also radius 1 engaging surfaces and the static surfaces 201A-201D are also carpal 2 and 3 engaging surfaces.

All components of the invention can be used with bone growth materials, replacements, or simulators, including biologic and genetic drugs, coatings, or components.

The articulating surfaces 102A-D and 202A-D can include highly polished Cobalt Chromium. In other embodiments, polymers and ceramics such as pyrolytic carbon, polycarbon, or UHMWPE can be used, or a combination thereof.

As will be understood by one skilled in the art, various features of each of the different radial implants 100A-100D can be interchangeably used with the other implants 100A-100D. For example, while only implant 100B is illustrated as including the cutouts 151B, one of ordinary skill in the art will appreciate that the cutouts 151B can also be included in the stabilizing fin portion 150A of the radial implant 100A. Similarly, various features of each of the different carpal implants 200A-200D can be interchangeably used with the other implants 200A-200D. For example, while only the implant 200C is illustrated as including the stabilizing component 203C, one of ordinary skill in the art will appreciate that the implants 200A, 200B, and 200D can also include the stabilizing component 203C. One of ordinary skill in the art will also appreciate the advantages associated with providing each of the implants 100A-100D and each of the implants 200A-200D as unitary, single, one-piece, or monolithic implants.

A method of implanting the radial implant 100B and the carpal implant 200D will now be described. The description of the implantation of the radial implant 100B and the carpal implant 200D is for exemplary purposes only. Implantation of the other radial implants 100 is substantially similar to the implantation of radial implant 100B and will be readily understood by one of ordinary skill in the art from the description provided herein.

With reference to FIG. 10, the wrist joint is prepared to receive one or both of the implants 100B and 200D using the reamer 300, or any other suitable device for removing cartilage or tissue. If only the radial implant 100B is being implanted, then the reamer 300 can be provided with cutting features, such as cutting teeth, on only the side of the reamer 300 facing the radius 1. If only the carpal implant 200D is being implanted, then the reamer 300 can be provided with cutting features on only the side of the reamer 300 facing the carpal bones 2 and 3. The reamer 300 only clears cartilage or tissue. The reamer 300 is not used to resurface either the radius 1 or the carpal bones 2 and 3, as was done in previous wrist joint replacements methods. The reamer 300 is inserted into the joint space 5 on the radial side of the joint, as illustrated in FIG. 10.

With reference to FIG. 11, if the radial implant 100B is being implanted, then the slot 410 is formed in the radius 2 to receive the stabilizing fin 150B to anchor the implant 100B to the radius 2. If the carpal implant 200D is being implanted, then the slot 410 is formed in the scaphoid 2 to receive the stabilizing fin 250D for anchoring the implant 200D to the scaphoid 2. If both the radial implant 110B and the carpal implant 200D are being implanted, then the slot 410 is formed in both the scaphoid 2 and the radius 1.

The slot 410 can be formed using any suitable bone cutting device. For example, the slot 410 can be formed using a saw that is aligned with the radius 1 and/or the scaphoid 2 using alignment holes 420 formed in the radius 1 and/or the scaphoid 2 using a suitable bone preparation device. In contrast to prior wrist replacement procedures in which a portion of the radius 1, scaphoid 2, and/or lunate 3 that is proximate to the joint space 5 is reshaped or resected, surfaces of the radius 1, the scaphoid 2, and/or the lunate 3 facing the joint 5 are not resected or reshaped to form the slot 410. The slot 410 simply provides a recess in the radius 1 and/or scaphoid 2 to allow the implants 100B and 200D to be anchored to the radius 1 and/or the scaphoid 2 respectively. The slot 410 is formed in the side of the radius 1 opposite to the ulna 4 and in the side of the scaphoid 2 opposite to the lunate 3.

After the slot 410 is formed, the carpal implant 200D and/or the radial implant 100B are implanted. The carpal implant 200D is implanted such that the stabilizing fin 250D is laterally inserted into the slot 410 of the scaphoid 2 from the radial side of the wrist joint. Similarly, the radial implant 100B is implanted such that the stabilizing fin 150B is laterally inserted into the slot 410 of the radius 1 from the radial side of the wrist joint. The implants 200D and 100B can be secured in the slot 410 using any suitable device or method. For example, if the implants 200D and 100B include the cutouts 151B and 251D, the cutouts can receive bone growth or tissue growth to help anchor the implants 200D and 100B. Bone cement or any other suitable adhesive can also be used to anchor the implants 200D and 100B.

Implantation of the carpal implants 200A-200C does not require formation of the slot 410. For example, with reference to FIG. 13, the spacer 230A of the carpal implant 200A can be inserted within the joint space 5 with the spacer 230A positioned between the scaphoid 2 and the lunate 3. A suitable fastening device, such as the pin 220, can be inserted through the spacer 230A and into cooperation with the scaphoid 2 and/or the lunate 3 to secure the carpal implant 200A into position. The pin 220 can be similarly used to engage the spacers 230B and 230C of the implants 200B and 200C respectively to secure the implants 200B and 200C into position.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A wrist arthroplasty system comprising:
   a monolithic carpal implant for resurfacing carpal bones having a concave, arcuate carpal engaging surface that at least substantially corresponds to the natural shape of carpal bones and a convex, arcuate carpal articulating surface that is opposite to said engaging surface;
   the carpal engaging surface includes a continuous circular arc that is co-incident with the carpal articulating surface; and
   a radial implant for resurfacing a radius bone having a concave, radial articulating surface operable to articulate with said carpal articulating surface, a convex radial engaging surface opposite to said radial articulating surface, and a first radial stabilizing fin extending from said radial engaging surface.

2. The wrist arthroplasty system of claim 1, said carpal engaging surface further comprising a spacer sized to fit between a scaphoid bone and a lunate bone; and
   a fastening device extending through said spacer, said fastening device operable to secure said carpal implant to at least one of the scaphoid bone and the lunate bone.

3. The wrist arthroplasty system of claim 1, further comprising a stabilizing component extending from an end of said carpal engaging surface.

4. The wrist arthroplasty system of claim 1, further comprising a carpal stabilizing fin extending from said carpal engaging surface that is operable to anchor said carpal implant to a scaphoid bone;
   wherein said stabilizing fin further comprises apertures.

5. The wrist arthroplasty system of claim 1, further comprising a protrusion portion extending from an end of said radial engaging surface, said protrusion portion operable to articulate with an ulna bone;
   wherein said concave radial articulating surface further comprises a protruding portion.

6. A wrist arthroplasty system comprising:
   a monolithic carpal implant having a main carpal body with a carpal engaging surface on a first side of the main body and a carpal articulating surface on a second side of the main body, said first side is opposite to said second side;
   the carpal engaging surface includes a continuous circular arc that is co-incident with the carpal articulating surface; and
   a radial implant having a main radial body with a radial engaging surface on a first side of the main radial body and a radial articulating surface on a second side of said main radial body, said first side is opposite to said second side;
   wherein said carpal articulating surface articulates directly with said radial articulating surface.

7. The wrist arthroplasty system of claim 6, wherein said carpal articulating surface has an arcuate shape that corresponds to an arcuate shape of said radial articulating surface.

8. The wrist arthroplasty system of claim 6, wherein said carpal implant further comprises a carpal stabilizing fin extending from said carpal engaging surface.

9. The wrist arthroplasty system of claim 8, wherein said carpal stabilizing fin includes a first planar surface and a second planar surface opposite said first planar surface, said first and second planar surfaces are perpendicular to said carpal engaging surface.

10. The wrist arthroplasty system of claim 6, wherein said radial implant further comprises a radial stabilizing fin extending from said radial engaging surface.

11. The wrist arthroplasty system of claim 10, wherein said radial stabilizing fin further comprises a first planar surface and a second planar surface opposite said first planar surface, said first planar surface and said second planar surface are each perpendicular to said radial engaging surface.

12. A wrist arthroplasty system comprising:
    a monolithic carpal implant having a main carpal body with a carpal engaging surface on a first side of said main carpal body and a carpal articulating surface on a second side of said main carpal body, said first side is opposite to said second side, said carpal engaging surface having a spacer extending from said carpal engaging surface sized to fit between a scaphoid bone and a lunate bone;
    the carpal engaging surface includes a continuous circular arc that is co-incident with the carpal articulating surface; and
    a radial implant having a main radial body with a radial engaging surface on a first side of said main radial body and a radial articulating surface on a second side of said main radial body, said first side is opposite to said second side;
    wherein said carpal articulating surface articulates directly with said radial articulating surface.

13. The wrist arthroplasty system of claim 12, wherein said carpal engaging surface has a concave arcuate carpal engaging shape that at least substantially corresponds to a natural shape of carpal bones and said spacer extends from said concave carpal engaging surface.

14. The wrist arthroplasty system of claim 13, further comprising a fastening device extending through said spacer, said fastening device operable to secure said carpal implant to at least one of the scaphoid bone and the lunate bone.

15. The wrist arthroplasty system of claim 13, further comprising a stabilizing component extending from said concave carpal engaging surface to secure an edge of one or more carpal bones.

16. The wrist arthroplasty system of claim 13, further comprising a carpal stabilizing fin extending from said concave carpal engaging surface to anchor said carpal implant to a scaphoid bone, said stabilizing fin further comprises apertures passing through said stabilizing fin.

17. The wrist arthroplasty system of claim 12, wherein the radial implant further includes a protrusion extending from said radial engaging surface operable to articulate with an ulna bone.

18. The wrist arthroplasty system of claim 12, wherein said radial implant further includes a radial stabilizing fin extending from said radial engaging surface.

19. The wrist arthroplasty system of claim 18, wherein said radial stabilizing fin further comprises a first planar surface and a second planar surface opposite said first planar surface, said first planar surface and said second planar surface are each perpendicular to said radial engaging surface.

20. The wrist arthroplasty system of claim 12, wherein said radial implant further includes a first stabilizing fin and a second stabilizing fin spaced apart from the first stabilizing fin and extending from said radial engaging surface.

* * * * *